(12) United States Patent
Faccioli et al.

(10) Patent No.: US 12,059,355 B2
(45) Date of Patent: Aug. 13, 2024

(54) CONSTRAINED SPACER DEVICE FOR THE KNEE

(71) Applicant: TECRES S.p.A., Sommacampagna (IT)

(72) Inventors: Giovanni Faccioli, Monzambano (IT); Renzo Soffiatti, Nogara (IT)

(73) Assignee: TECRES S.P.A., Sommacampagna (IT)

( * ) Notice: Subject to any disclaimer, the term of this patent is extended or adjusted under 35 U.S.C. 154(b) by 612 days.

(21) Appl. No.: 16/300,197

(22) PCT Filed: May 10, 2017

(86) PCT No.: PCT/IB2017/052719
§ 371 (c)(1),
(2) Date: Nov. 9, 2018

(87) PCT Pub. No.: WO2017/199131
PCT Pub. Date: Nov. 23, 2017

(65) Prior Publication Data
US 2019/0216607 A1    Jul. 18, 2019

(30) Foreign Application Priority Data

May 16, 2016 (IT) .......................... 102016000050136

(51) Int. Cl.
*A61F 2/38* (2006.01)

(52) U.S. Cl.
CPC .......... *A61F 2/3836* (2013.01); *A61F 2/3859* (2013.01); *A61F 2/389* (2013.01); *A61F 2/3877* (2013.01); *A61F 2230/0006* (2013.01)

(58) Field of Classification Search
CPC ........ A61F 2/38; A61F 2/3836; A61F 2/3859; A61F 2/389; A61F 2/3868
See application file for complete search history.

(56) References Cited

U.S. PATENT DOCUMENTS

| | | | |
|---|---|---|---|
| 4,216,549 A | 8/1980 | Hillberry et al. | |
| 4,224,697 A * | 9/1980 | Murray | A61F 2/3836 623/20.25 |
| 5,123,928 A | 6/1992 | Moser | |
| 5,282,867 A * | 2/1994 | Mikhail | A61F 2/0811 623/13.12 |
| 10,299,932 B2 * | 5/2019 | Faccioli | A61F 2/3804 |
| 2016/0166284 A1 * | 6/2016 | Hacking | A61L 27/18 604/892.1 |
| 2018/0008424 A1 * | 1/2018 | Collazo | A61F 2/4684 |

FOREIGN PATENT DOCUMENTS

DE    102014204326    9/2015

OTHER PUBLICATIONS

International Search Report dated Aug. 24, 2017 for PCT/IB2017/052719 (3 pages).

* cited by examiner

*Primary Examiner* — Ariana Zimbouski
*Assistant Examiner* — Christine L Nelson
(74) *Attorney, Agent, or Firm* — Tutunjian & Bitetto, P.C.

(57) ABSTRACT

Spacer device for the knee joint comprising a tibial component, adapted to be fixed to one end of the tibial bone in proximity to the knee joint, and a femoral component, adapted to be fixed to one end of the femoral bone in proximity to the knee joint, wherein the tibial component is adapted to come into contact and be articulated with the femoral component, wherein the tibial component includes a protrusion adapted to be inserted in an opening present in the femoral component; method for the assembly of the spacer device.

20 Claims, 6 Drawing Sheets

CONSTRAINED SPACER DEVICE FOR THE KNEE

TECHNICAL FIELD OF THE INVENTION

The present invention refers to a constrained spacer device adapted to be implanted at a knee joint.

STATE OF THE PRIOR ART

As is known, joint prostheses, after having been implanted in the human body, can be removed, for example due to an infection that arose at the implant site.

In order to treat the infection, it is possible to temporarily substitute the infected prosthesis with a spacer device provided with suitable antibiotic medications, so to be able to proceed with a new prosthetic implant once the site in question has healed.

Such spacer device is capable of maintaining the articular space necessary for the implant of a new prosthesis, so as to prevent the shortening of the tissues, the atrophying of the articulation and the loss of muscle tone, in addition to—as stated—containing medical agents capable of treating the tissues surrounding it.

However, when the implant site is particularly weak or damaged, or when the substitution of an infected prosthesis occurs for a second time, it is necessary to use a constrained spacer device, in which its femoral and tibial components are connected or constrained to each other. Document U.S. Pat. No. 5,282,867 discloses an example of a hinged prosthesis.

It is therefore necessary to arrange a preformed spacer device, capable of providing the aforesaid constraint between the components thereof.

SUMMARY OF THE INVENTION

One object of the present invention is to improve the state of the prior art.

A further object of the present invention is to provide a constrained spacer device, possibly also secondary, adapted to treat an infection that arose at the implant site, in particular for the knee joint.

A still further object of the present invention is to provide a constrained spacer device that is pre-formed and simultaneously able to allow a good mobility for the patient.

A further object of the present invention is to provide a constrained spacer device that ensures a high stability for the knee joint.

In accordance with one aspect of the present invention, a constrained spacer device for a knee is provided according to the present application.

The present invention further refers to a method for the assembly of a constrained spacer device for a knee according to the present application.

The present application refers to preferred and advantageous embodiments of the invention.

BRIEF DESCRIPTION OF THE DRAWINGS

Further characteristics and advantages of the present invention will be more evident from the detailed description of a preferred but not exclusive embodiment of a constrained spacer device for a knee, illustrated as a non-limiting example in the enclosed drawing tables in which.

DETAILED DESCRIPTION OF THE INVENTION

Figure 1:
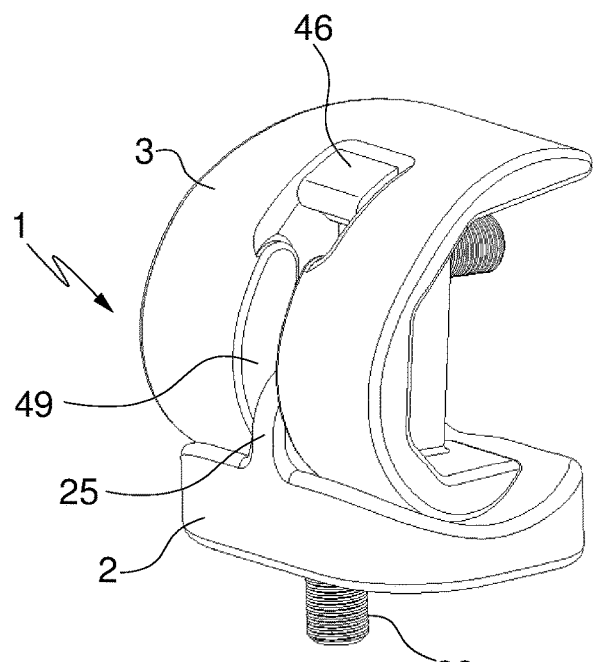
FIG. 1 and FIG. 2 are perspective views of the spacer device according to the present invention that illustrate two mutual positions of a femoral component with respect to a tibial component.
Figure 2:
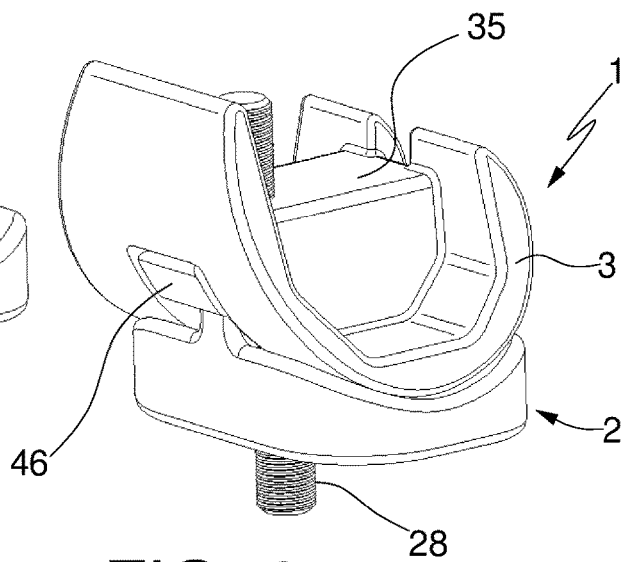
Figure 3:
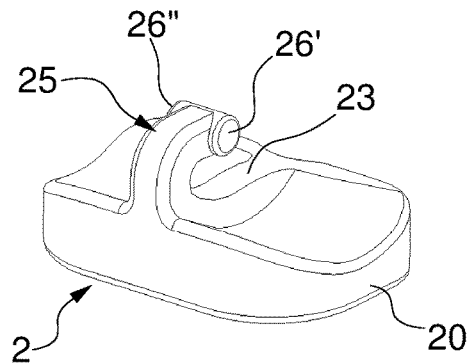
FIGS. 3 to 5 are respectively a lateral perspective view, a top view and a bottom perspective view of the tibial component of the spacer device according to the present invention.

With reference to the enclosed figures, reference number 1 generically indicates a constrained spacer device.

Such spacer device is temporary, preformed, and adapted to be implanted at the knee joint.

Such spacer device is during use adapted to be implanted at the knee joint in substitution of a preceding prosthesis, and it is during use adapted to treat an infection underway in the knee joint itself.

By constrained spacer device it is intended a spacer device whose tibial and femoral components are joined together, i.e. they are hinged, or it is not possible to modify the relative distance from one to the other.

In substance, the femoral component is capable of rotating and translating with respect to the tibial component (and vice versa) but the two components cannot be separated from each other. This serves so that, once the two components are fixed to the bone of the patient during implant, the knee joint cannot undergo dislocations, or that tibia and femur do not have irregular relative rotation.

The femoral component and the tibial component of the spacer device 1 according to the present invention, according to that defined now and as will be better understood in the course of the present description, are constrained to each other in an articulated manner, and they are both adapted to be stably fixed to the respective bone of the patient.

The spacer device 1 according to the present invention comprises a tibial component 2 and a femoral component 3.

The tibial component 2 is adapted to be fixed to the end of the tibial bone at the knee joint while the femoral component 3 is adapted to be fixed to the end of the femoral bone in proximity to the knee joint.

In one version of the invention, only the femoral component 3 and the tibial component 2 are present, constrained to each other, while no patellar component is present, since it is not necessary for the operation of the spacer device, and since it is desirable that the latter be as simple as possible.

The tibial component 2 comprises a tibial plate 20, on which the femoral component 3 is adapted to abut, roll and/or slide and with which it is articulated.

The tibial plate 20 comprises two condylar articular bases 21, 22.

The condylar articular bases 21, 22 are substantially concave and have a curvature radius R2.

The tibial component 2 further comprises, between the condylar articular bases 21, 22, a rib 23.

Such rib 23 is in relief with respect to the surface of the tibial plate 20 and/or of the condylar articular bases 21, 22.

At its front portion, the tibial component 2 and/or the rib 23 has a protrusion 25. Such protrusion 25 has a substantially curved and/or C-shaped or swan-neck projection and during use is projected upward or towards the femoral component 3.

The protrusion 25 has a head or end 26 that is substantially T-shaped.

Specifically, the protrusion 25 comprises, as stated, a substantially curved shape and/or C shape comprising a first section that corresponds with at least part of the rib 23, a second section, with substantially vertical section, and a third section, raised with respect to the rib 23, but which is substantially parallel to the latter.

Such third section departs from the second section and terminates with the head or end 26, shaped as a T.

In one version of the invention, the rib 23 is not present and therefore the protrusion 25 only has a section with substantially vertical progression, from which a further section departs, substantially parallel to the tibial plate 20 and which terminates with the head or end 26.

The third section or the further section of the protrusion 25 is extended towards the rear part of the tibial component 2.

Therefore, the head or end 26 of the protrusion 25 comprises two sections 26', 26" that are extended on opposite sides with respect to the third section (and/or to the protrusion 25). In one version of the invention, the two sections 26', 26" are lateral bulges of the protrusion 25 or of its third section.

The sections 26', 26" have a progression that is laterome-dial or parallel to the transverse axis of the human body.

The transverse axis of the human body is an axis of the human body that goes from right to left.

Due to the shape of the protrusion 25, the head or end 26 thereof comes to be situated in raised position substantially at the center of the tibial plate 20 and/or of the rib 23.

Figure 15:
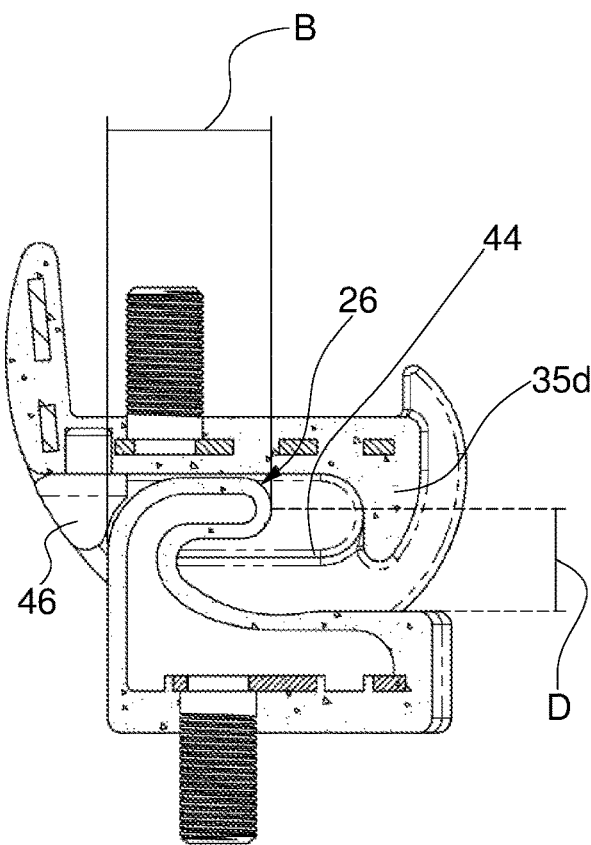
Figure 16:
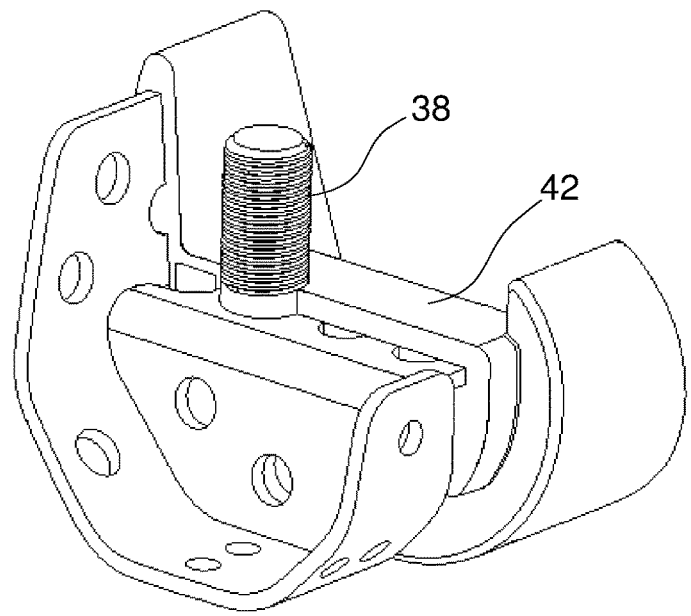
FIG. 16 is a rear side perspective view of the femoral component, partially sectioned, according to one version of the invention, in which its internal core is visible.
Figure 17:
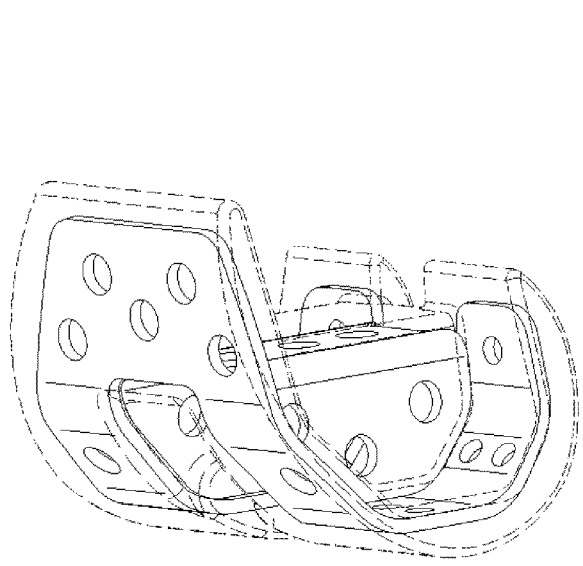
FIGS. 17 and 19 are front side perspective views, partially transparent, respectively of the femoral component and of the tibial component of the spacer device according to one version of the invention.
Figure 18:
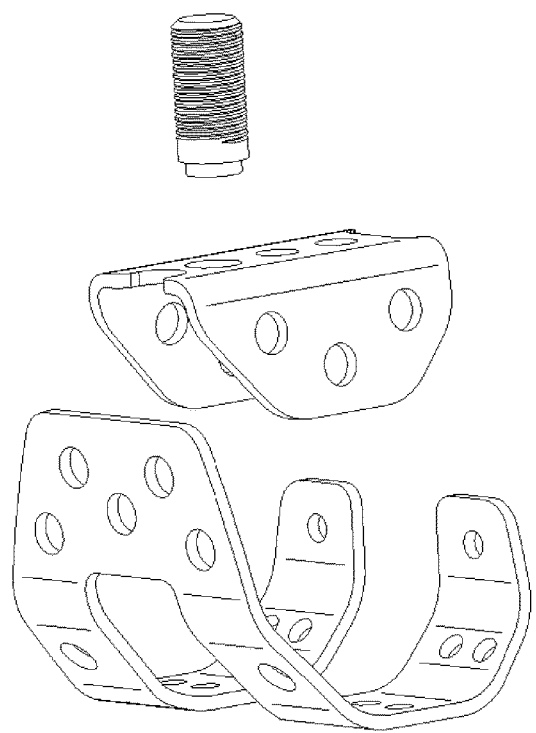
FIGS. 18 and 20 are front side perspective views respectively of the internal core of the femoral component and of the tibial component of the spacer device according to one version of the invention.
Figure 19:
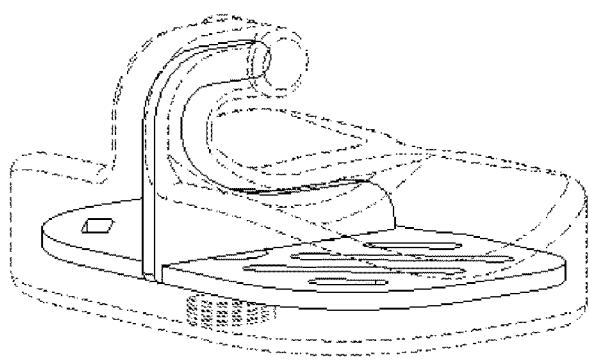
Figure 20:
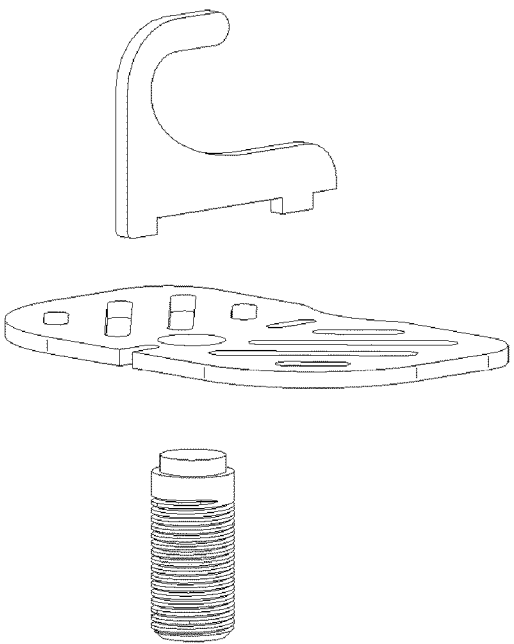

In particular, as visible in FIG. 15, the head or end 26 is situated at a distance D from the rib 23 or at a distance B from the most-front part of the tibial plate 20 and/or of the tibial component 2.

Figure 4:
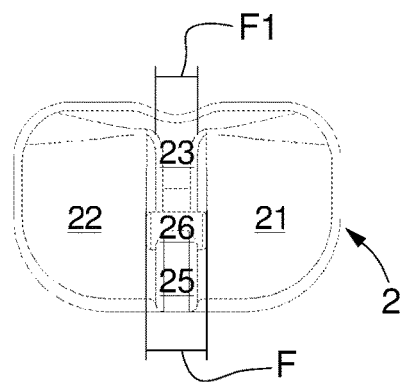
Figure 5:
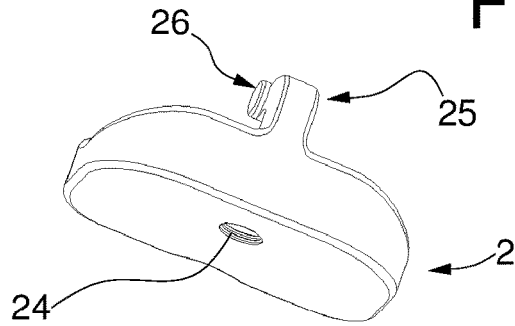
Figure 6:
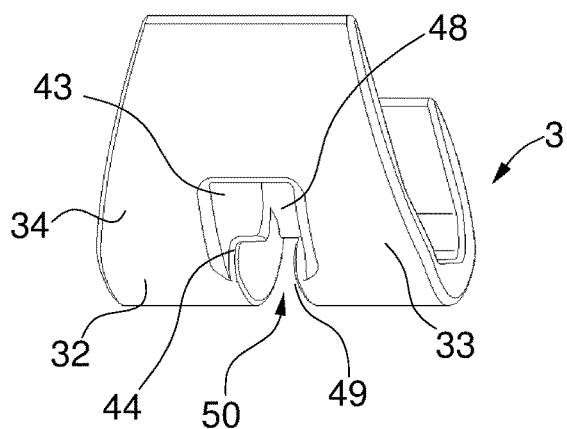
FIGS. 6 to 9 are respectively a lateral perspective view, a top view, a bottom front view and a bottom rear view of the femoral component of the spacer device according to the present invention.
Figure 7:
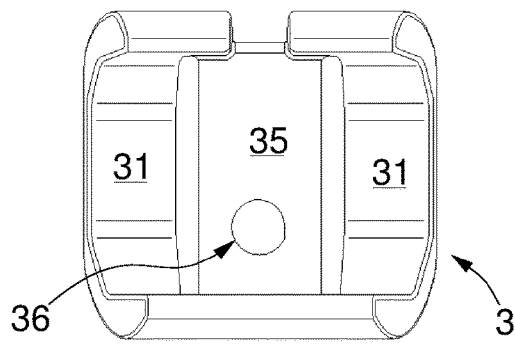

As visible in FIG. 4, the head or end 26, including the sections 26', 26", has a size or width, calculated according to the transverse axis of the human body, equal to F.

In particular, F is greater than the width F1 of the rib 23 (or of the protrusion 25).

The width of the first and/or second and/or third section or of the section with substantially vertical progression and/or of the further section of the protrusion 25 also have a width substantially corresponding to F1.

The tibial component 2, along a surface adapted to come into contact with the tibial bone of the patient or in any case opposite the condylar articular bases 21, 22, has a hole 24.

The hole 24 is adapted to house and fix, through for example a screw-nut screw coupling, at least one pin 28.

The at least one pin 28, possibly threaded, is a pin adapted for the connection, the fixing and/or the centering or the orientation of the tibial component 2 with respect to the bone end of the tibial bone of the patient.

The at least one pin 28 is extended from the face of the tibial component 2 opposite that which has the two condylar articular bases 21, 22.

The protrusion 25, during use, is adapted to be inserted in the femoral component 3, in a manner such to create a guided articulation or a constraint articulation between the femoral component 3 and the tibial component 2.

The femoral component 3 has a shape that generally reproduces the condylar articulation surfaces of the femur.

Figure 12:
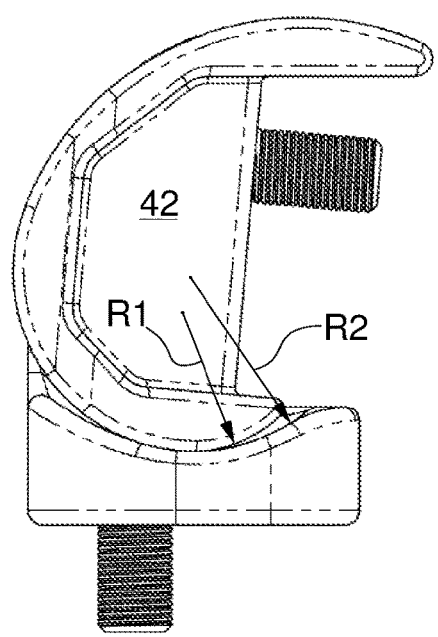
FIGS. 12 and 13 are side views of the spacer device according to the present invention that illustrate two mutual positions of the femoral component with respect to the tibial component.
Figure 13:
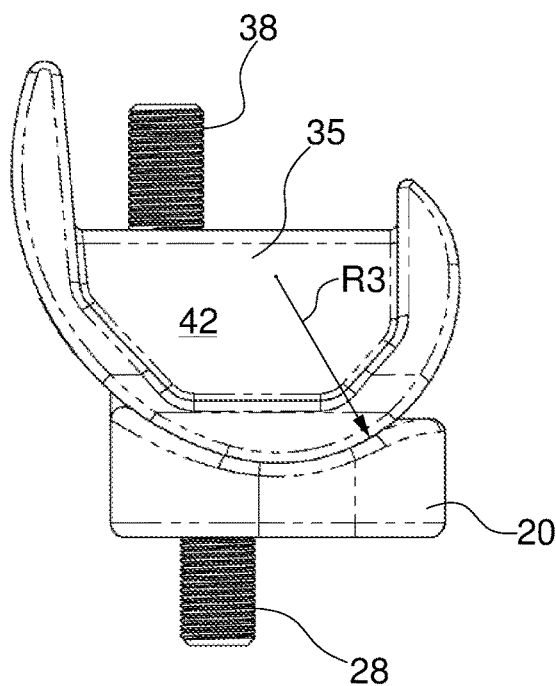

In particular, the femoral component 3 has, as is visible for example in FIGS. 12 and 13, a substantially U-shaped form—in cross section according to a plane parallel to the sagittal plane of the human body.

The femoral component 3 comprises an internal surface 31, substantially concave, adapted to be positioned in contact with the bone seat, and an external surface 32, substantially convex, adapted to come into contact and be articulated with the tibial component 2.

The femoral component 3 is symmetric, with respect to a plane of symmetry parallel to the sagittal plane of the human body.

More in detail, the femoral component 3 comprises a first condylar portion 33 placed laterally and a second condylar portion 34 medially placed with respect to the sagittal plane of the human body, each having a shape similar to that of the condyles of the knee.

The condylar portions 33, 34 in turn have a substantially U-shaped form—in cross section according to a plane parallel to the sagittal plane of the human body.

The condylar portions 33, 34, in their front during use portion of the spacer device 1 according to one version of the present invention, converge towards each other and are joined together to form a joining portion or surface adapted to come into contact with the patella or to be arranged substantially in the zone where it is usually situated from the anatomical standpoint.

The condylar portions 33, 34 are articulated on the condylar articular bases 21, 22 of the tibial component 2.

The condylar portions 33, 34 are separated from each other by an intercondylar space 50. The intercondylar space 50 is extended at least along the rear and central during use portion of the femoral component 3 and/or of the condylar portions 33, 34. In one version of the invention, the intercondylar space 50 is also extended for a portion of the front part of the femoral component 3, e.g. the portion which, during use, is placed downward and towards the central portion thereof.

The femoral component 3 comprises a box element 35, placed on the internal surface 31.

The box element 35 is connected to the internal surface 31 and, in one version of the invention, is integrally made therewith and/or with the femoral component 3.

The box element 35 has two lateral walls and one connector wall, which connects and joins the lateral walls. The connector wall is placed above the lateral walls of the box element. The lateral walls have a progression parallel to the sagittal plane of the human body. During use, they are extended therefore from the front portion to the rear portion of the internal surface 31 of the tibial component 3.

The box element 35 has a substantially overturned U shape—in cross section according to a plane parallel to the front plane of the human body.

Between the lateral walls and the connector wall of the box element 35, a seat or cavity is comprised or enclosed, corresponding to the abovementioned intercondylar space 50.

At the connector wall of the box element 35, a hole 36 and/or a cylindrical protrusion or stem 38 (possibly threaded) can be present, for the connection, the fixing and/or the centering or the orientation of the femoral component 3 with respect to the bone end of the femoral bone.

The condylar portions 33, 34 have, in at least one portion of their profile, a curvature radius R1, as is visible for example in FIGS. 12 and 13.

The radius R1 is present at least in the rear portion of the condylar portions 33, 34.

In a further version of the invention, the condylar portions 33, 34 have, in at least one portion of their profile, a curvature radius R3, as is visible for example in FIGS. 12 and 13.

The radius R3 is present at least in the central portion of the condylar portions 33, 34.

The curvature radius R1, in one version of the invention, is smaller than the curvature radius R2.

In a further version, the curvature radius R3 is substantially equal to the curvature radius R2.

The box element 35 comprises an external surface 42 and an internal surface 43. The internal surface 43 faces towards the intercondylar space 50.

The internal surface 43 in turn comprises two internal lateral walls and one internal connector wall, which delimit the intercondylar space 50.

The internal connector wall is placed above the internal lateral walls of the box element. The internal lateral walls have a progression parallel to the sagittal plane of the human body. During use, therefore, they depart from the front portion to the rear portion of the internal surface 31 of the tibial component 3.

Each or at least one of the internal lateral walls of the internal surface 43 have a step 44. Such step 44 is projecting with respect to the internal lateral surface of the internal surface 43. Therefore, the step 44 is extended towards the intercondylar space 50.

Such step 44 constitutes a kind of guide for the head or end 26 of the tibial component 2. Indeed, such head or end 26, during the articulation of the femoral component 3 on the tibial component 2, slides and/or can rotate along such step 44, allowing the articulation of the knee of the patient in which the spacer device 1 has been implanted.

Simultaneously, the step 44 determines the constraint of the femoral component 3 with the tibial component 2, since the head or end 26 of the latter abuts against (particularly due to the sections 26', 26") and is substantially prevented—regarding its movements from right to left—from exiting from the seat determined by the box element 35 and/or, hence, from the intercondylar space 50.

In one version of the invention, such step 44 has a substantially overturned S shape.

Regarding such overturned S, during use: the upper horizontal section coincides with the internal connector wall, the concavity is placed at the rear part of the tibial component 3, the convexity is placed at the front part of the tibial component 3 and the lower horizontal second section coincides with the (central) external surface 42 of the femoral component 3.

The overturned S shape of the step 44 and/or the presence of the step 44 allows creating an opening, in the femoral component 3 and in particular between its two condylar portions 33, 34, comprising two portions and/or having two widths. By width, in this case, it is intended the size of the opening along a direction that goes from right to left, hence considered along the front plane of the human body or parallel to the same. Such direction is horizontal, i.e. also parallel to the abutment surface of the human body.

The opening determined by the box element 35 and by the step 44 coincides with the intercondylar space 50.

Figure 8:
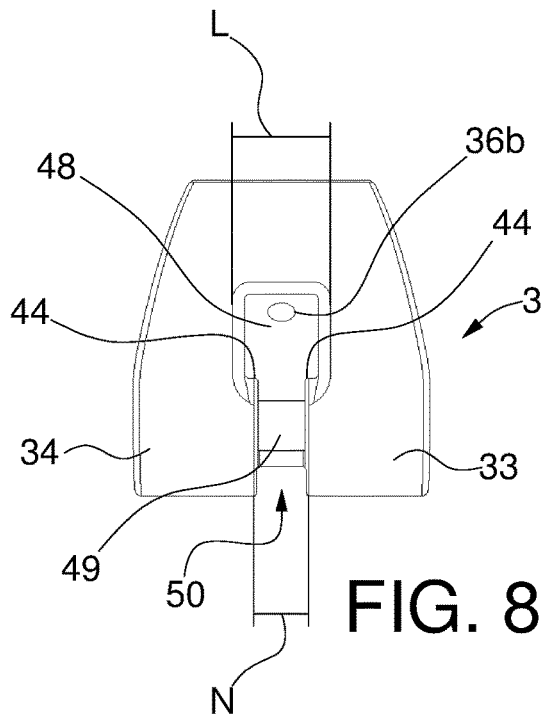
Figure 9:
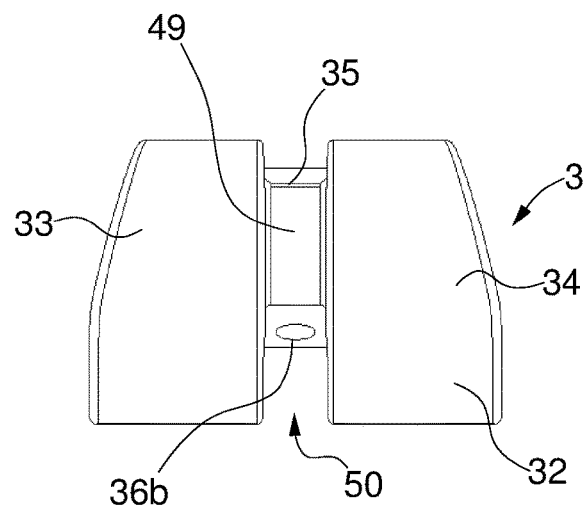
Figure 10:
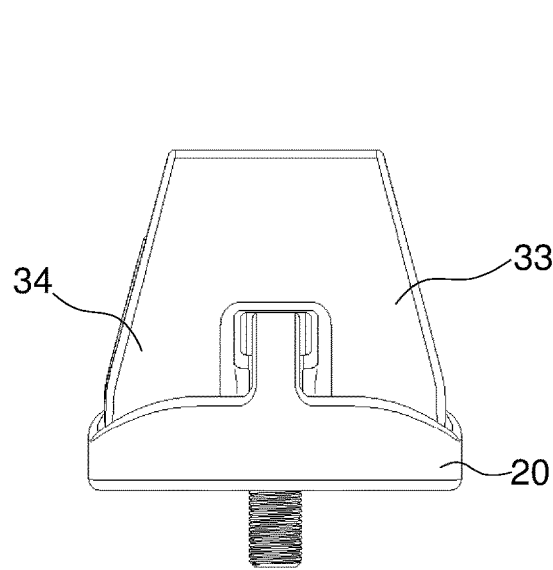
FIGS. 10 and 11 are front views of the spacer device according to the present invention, respectively not provided or provided with a further closure or locking element.
Figure 11:
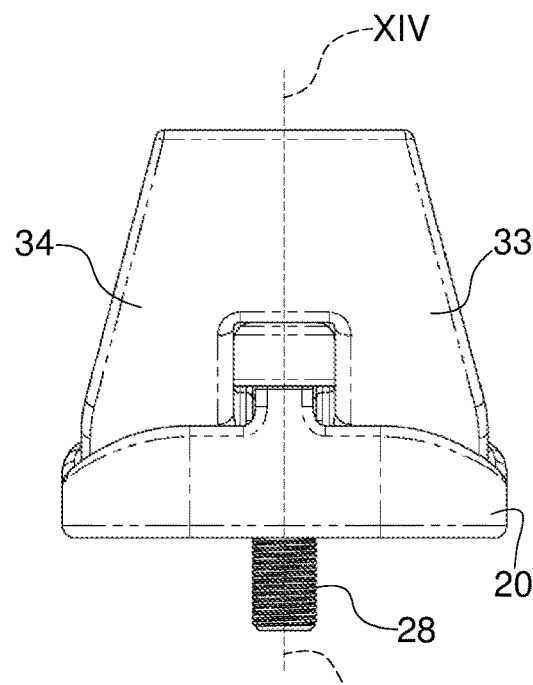

In particular, as is visible for example in FIG. 8, for example in proximity to the front zone of the femoral component 3, a first opening 48 is present having a width L.

In proximity instead to the central and lower zone of the femoral component 3, a second opening 49 is present which has a width N, in which N is smaller than L.

In particular, as will be better described hereinbelow, the width L corresponds substantially or is slightly greater than the width F of the head or end 26 of the femoral component 2. In such a manner, it is possible to insert such head or end 26 inside the intercondylar space 50, through such first opening 48.

Then, once the protrusion 25 is inserted, by means of its head or end 26, into the femoral component 3, the latter is engaged with, or at least abutted against, the step 44 and is unable to exit from the second opening 49 having width N.

Indeed, the width N is smaller than the width F and substantially corresponds to the width F1, or is slightly greater than the latter.

According to a section taken along a plane parallel to the front plane of the human body, therefore, the opening has a substantially T shape, substantially corresponding to the T shape of the protrusion 25 and/or of the head or end 26 of the protrusion 25.

The spacer device 1, according to at least one version of the invention, then comprises a closure or locking element 46.

The closure or locking element 46 has size substantially corresponding to that of the first opening 48 or at least of its initial part. In particular, such closure or locking element 46 is capable of closing the first opening 48 and preventing the exit of the head or end 26 from the intercondylar space 50 delimited by the box component 35 of the femoral component 3.

The closure or locking element 46 can be provided with a pin 47, adapted to be inserted, e.g. snap-inserted, in at least one hole 36*b* suitably made in the femoral component 3.

The hole 36*b* is placed at the front portion of the femoral component 3, in a manner so as to maintain the closure or locking element 46 in the front or frontal portion thereof.

The closure or locking element 46 has an internal face 46*d* (during use directed towards the bottom wall 35*d* of the box element 35) that is substantially concave. In such a manner, the sections 26', 26" can also rotate into such position of contact with the internal face 46*d*, and hence the femoral component 3 can also be articulated in this position with respect to the tibial component 2.

Figures 21, 22:
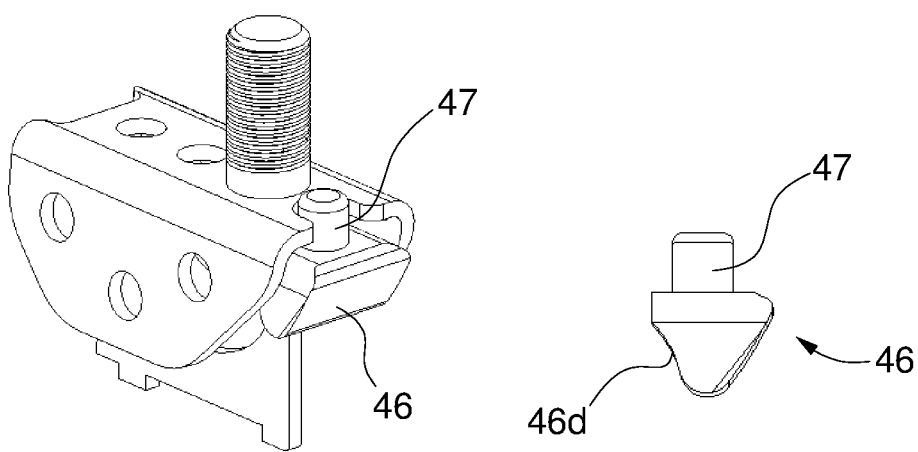
FIG. 21 is a front side perspective view of the internal core of the spacer device according to one version of the invention, in which the further closure or locking element is visible.
FIG. 22 is a front side view of the further closure or locking component of the spacer device according to the present invention.

The closure or locking element 46 substantially has a prism shape, e.g. with triangular base, as visible in FIG. 22.

Figure 14:
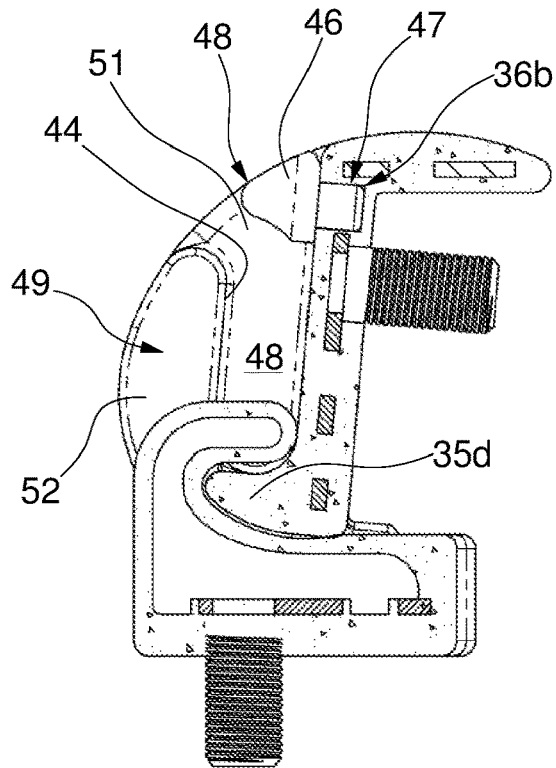
FIGS. 14 and 15 are sectional side views of the spacer device according to the present invention pursuant to FIGS. 12 and 13, taken along the trace plane XIV-XIV of FIG. 11.

Seen in cross section, i.e. in a section parallel to the sagittal plane of the human body, as illustrated in the FIGS. 14 and 15, the first opening 48 has a substantially wedge-like shape while the second opening 49 has a progression that is substantially wedge-shaped or L-shaped. In the latter version, for example, the sections of the L affect (the longer one) the central portion towards the bottom and (the shorter one) the rear portion of the femoral component 3, at its external surface 32.

In particular, the second opening 49 is a through opening, from front to rear of the femoral element 3.

The first opening 48, instead, is open at its front part. In the rear part, however, it is closed by the bottom wall 35*d* of the box element 35.

The bottom wall 35*d*, therefore, acts as a block for the sliding of the head or end 26 on the steps 44 and hence as a block for the maximum articulation of the femoral component 3 with respect to the tibial component 2.

The bottom wall 35*d* has a curvature substantially corresponding to that of the sections 26', 26" of the protrusion 25, in a manner so as to allow the rotation thereof—and hence the rotation of the femoral component 3 on the tibial component 2—even in such position.

The first and the second opening 48, 49 identify corresponding portions in the internal lateral walls of the box element 35.

Such portions are delimited, on each side, by the step 44.

In particular, the internal lateral walls have a first portion or surface 51 and a second portion or surface 52.

Both such portions have a progression substantially parallel to the sagittal plane of the human body. The first portion or surface 51, nevertheless, is placed more in proximity to the internal connector wall of the box element 35. In such a manner, it is situated more internally with respect thereto.

Such first portion or surface 51 has a progression that is substantially rectangular with smoothed edges. The height of such first portion or surface 51 is substantially equal to the bulk of each of the sections 26', 26".

The sections 26' and 26", in one version of the invention, are small cylinders which depart laterally from the protrusion 25. In a further version, the sections 26', 26" have a shape adapted to allow the rotation of the femoral component 3 on the tibial component 2, e.g. small balls, etcetera.

The sections 26', 26", in fact, act as a rotation hinge or axis around which a relative rotation occurs between the tibial component 2 and the femoral component 3. The second portion or surface 52 is instead more external with respect to the internal connector wall of the box element 35. In particular, such second portion or surface 52 is closer to the tibial component 2, with respect to the first 51.

This second portion or surface 52 has a substantially L-shaped progression, in which its larger section is substantially parallel to the progression of the first portion or surface 51, while its shorter section continues upward in a substantially perpendicular manner, considering the spacer device 1 during use.

The distance between the first portions or surfaces 51 is equal to L while the distance between the two second portions or surfaces 52 is equal to N.

As is visible in FIGS. 16 to 20, the spacer device 1 according to the present invention can comprise an internal core, having shape substantially corresponding to that of the tibial 2 and femoral 3 components.

The spacer device 1 according to the present invention can be porous and comprise at least one medical substance, such as an antibiotic, adapted to be released in the tissues surrounding the spacer device, in order to combat the infection.

The closure or locking element 46, at least in one version of the invention, determines the front wall of the box element 35.

As is seen, the present invention allows attaining the pre-established objects, since it allows treating the infection underway at the surgical site, simultaneously allowing a rotational-translational movement of the femoral component on the tibial component.

For such reason, therefore, the spacer device 1 comprises means for sliding and rotating the femoral component 3 on the tibial component 2 and vice versa. The rotation and sliding or translation movement is a relative movement of the femoral component 3 on the tibial component 2.

Such means, in at least one version of the invention, are constituted by the protrusion 25, with its head or end 26 and by the opening or intercondylar space 50 of the femoral component 3, possibly defined by the presence of the step 44.

Such rotational-translational or sliding and rotation movement cannot laterally translate, but only in front-rear direction, since the femoral component is constrained in an articulated manner to the tibial component.

The device according to the present invention, therefore, follows the physiological movement of the knee joint.

The closure or locking element 46 can be removed from the spacer device 1, for example when the latter must be removed from the human body in order to allow the implant of a new permanent prosthesis.

The spacer device 1, according to a non-limiting version of the invention, is assembled according to the following method: arranging a tibial component 2 and a femoral component 3 as described above and inserting or housing the protrusion 25 of the tibial component inside an opening present in the femoral component 3.

In particular, the head or end 26 of the tibial component 2 is inserted in the first opening 48 of the femoral component 3. Then, the sections 26', 26" abut against a step 44 placed on both sides of the opening of the femoral component 3, and they can slide on the step itself.

In this manner, the protrusion 25 can slide and traverse the second opening 49 of the femoral component 3. Simultaneously, the latter is articulated with the tibial component by rotating and/or translating thereon.

Finally, the closure or locking element 46 is inserted in the femoral component 3, for example in a hole 36*b* thereof, in a manner so as to prevent the protrusion 25 from exiting from the femoral component 3. In such a manner, the femoral component 3 and the tibial component 2 are constrained to each other in an articulated manner. The at least one pin 28 and/or the cylindrical protrusion or stem 38 can then be inserted or screwed, in a manner so as to stabilize (during use) the application respectively of the tibial component 2 on the tibial bone and/or of the femoral component 3 on the femoral bone.

Finally, it is possible to block the closure or locking element 46 by means of bone cement.

Once it is desired to extract the spacer device 1, it will suffice to remove the bone cement that locks and fixes the closure or locking element 46 in position, for example by means of a small scalpel, so to be able to remove it and free the passage for the protrusion 25. By making the latter exit from the first opening 48, it will be possible to release tibial and femoral component and then remove both the components (or at least one) from the infection site without having to overly compromise the residual tissues of the articulation of the patient.

As was seen above, the spacer device 1, even if implanted in situations of serious bone loss and loosening of the ligaments as well as in less damaged situations, is constrained, thus ensuring good stability to the knee joint.

In addition, the spacer device according to the present invention can therefore, during use, be implanted in the two affected bone ends and be constrained after implant of the femoral and tibial components. Indeed, once the femoral component and tibial component are implanted, it is possible to insert the protrusion 25 in the suitable space or opening of the femoral component. The access point of the protrusion in the femoral element is then closed by the presence of the closure or locking element.

A facilitated method is thus obtained, with advantages in terms of reduction of time and pain, both for the patient and for the doctor.

In addition, due to this the patient can lead a self-sufficient life for the entire period of use of the constrained spacer device according to the present invention.

The spacer component 1 according to the present invention is made of biologically compatible manner.

Such biologically compatible manner can be selected from among metals, metal alloys and organometallic compounds.

Alternatively, the biologically compatible manner can be selected from among ceramics, resins with high porosity, plastic materials and/or a combination thereof. Specifically, the aforesaid plastic materials can be selected from among thermoplastic polymers, such as acrylic resins, polyethylene, polypropylene, polyester, thermoformable polymers and other similar materials.

In one version of the present invention, the biologically compatible manner is a bone cement, e.g. polymethylmethacrylate (PMMA).

The presence of an internal core, e.g. metallic, can be particularly useful when the spacer device 1 is made of plastic or ceramic material.

In such a manner, it is possible to confer a greater stability to the implant, a higher load strength, etcetera.

In one version of the invention, the spacer device 1 is made of PMMA or the internal core is metallic and covered with PMMA.

As stated, the aforesaid biologically compatible manner, due to its porosity, can be impregnated with pharmaceutical and/or therapeutic products, such as antibiotics, before its use, by the producer and/or by the doctor before implant.

The invention thus conceived is susceptible to numerous modifications and variations, all falling within the scope of the inventive concept.

In addition, all the details can be substituted by other technically equivalent elements. In practice, the materials used, as well as the contingent shapes and sizes, can be of any type in accordance with requirements, without departing from the protective scope of the following claims.

The invention claimed is:

1. A temporary spacer device, configured to be implanted at a knee joint for replacing a previous prosthesis and configured to treat an infection at the knee joint itself, comprising:
    a tibial component, adapted to be fixed to one end of a tibial bone in proximity to the knee joint, wherein said tibial component comprises a tibial plate provided with two condylar articular bases and a rib placed between said condylar articular bases, and
    a femoral component, adapted to be fixed to one end of a femoral bone in proximity to the knee joint, wherein said femoral component has an opening and wherein said tibial component is adapted to come into contact and be articulated with said femoral component, wherein said two condylar articular bases are adapted to come into contact and be articulated with said femoral component,
    wherein said tibial component comprises a C-shaped protrusion adapted to be inserted in the opening present in said femoral component, in order to allow the sliding and the rotation of said femoral component on said tibial component, wherein said C-shaped protrusion has a curved longitudinal axis and comprises a first section that corresponds with the rib, a second vertical section and a third section raised with respect to and parallel to the rib and terminating with a T-shaped head affixed at a distal end of the C-shaped protrusion,
    wherein the first section has a first end located at a terminal edge of the tibial plate and a second end meeting the second vertical section,
    wherein said first section, said second vertical section and said third section define an opening having a longitudinal axis commencing from the terminal edge of the tibial plate to the second vertical section,
    wherein said T-shaped head is integral with the C-shaped protrusion and comprises two opposing sections which each extend opposite from each other in a direction perpendicular with respect to the curved longitudinal axis of said C-shaped protrusion and wherein said opening comprises a first opening having width (L) and a second opening having width (N), wherein (L) is greater than (N).

2. The spacer device according to claim 1, comprising means for sliding and rotation of said femoral component on said tibial component, wherein said means for sliding and rotation of said femoral component on said tibial component comprise at least said protrusion.

3. The spacer device according to claim 1, wherein said tibial component comprises a tibial plate provided with two condylar articular bases and a rib placed between said condylar articular bases, wherein said condylar articular bases are adapted to come into contact and be articulated with said femoral component.

4. The spacer device according to claim 1, wherein said femoral component has a U-shaped form in cross section according a plane parallel to the sagittal plane of the human body and comprises a concave internal surface in contact with the femoral bone seat, and a convex external surface adapted to come into contact with said tibial component.

5. The spacer device according to claim 4, wherein said femoral component comprises a first and a second condylar portion, said first condylar portion being laterally placed and said second condylar portion being medially placed with respect to the sagittal plane of the human body, said condylar portions having a U-shaped conformation in cross section according to a plane parallel to the sagittal plane of the human body, wherein said first condylar portion and said second condylar portion are separated from each other by an intercondylar space.

6. The spacer device according to claim 5, wherein said femoral component comprises a box element, placed on the internal surface of said femoral component, wherein said box element comprises two lateral walls, a connector wall connected to said lateral walls, wherein said walls identify an internal connector wall and two internal lateral walls which delimit said intercondylar space.

7. The spacer device according to claim 6, further comprising a step placed on each internal lateral wall of said box element and wherein each internal lateral wall of said box element comprises a step, wherein each step provides relative sliding and rotation of said femoral component on said tibial component, wherein each step delimits a first portion or surface and a second portion or surface of each internal lateral wall, wherein each first portion or surface is placed in proximity to the internal connector wall of the box element while each second portion or surface is placed in proximity to said tibial component.

8. The spacer device according to claim 7, wherein each of said first portions or surfaces are separated by a distance (L) while each of said second portions or surfaces are separated by a distance (N) of said intercondylar space or of said respective first opening and said second opening.

9. The spacer device according to claim 7, wherein said step has an S conformation and wherein said first opening is delimited by a bottom wall of said box element.

10. The spacer device according to claim 7, wherein each first portion or surface has a height equal to width of said two sections.

11. The spacer device according to claim 7, wherein each second portion or surface is L-shaped, having a larger section which is parallel to each first portion or surface, and a shorter section which continues in a perpendicular manner, considering the arrangement of said spacer device during use.

12. The spacer device according to claim 1, wherein said one head or end provided with two sections has a width (F) and wherein said protrusion has a width (F1), wherein said width (F) corresponds to or is slightly smaller than said width (L) and wherein said width (F1) corresponds to or is slightly smaller than said width (N).

13. The spacer device according to claim 1, comprising a closure or locking element adapted to close said first opening and to prevent the exit of said protrusion from said opening of said femoral component.

14. The spacer device according to claim 1, wherein said femoral component and said tibial component have an internal core made of metal.

15. The spacer device according to claim 1, wherein said spacer device is made of biologically compatible material selected from among a metal, a metal alloy, or an organometallic compound.

16. The spacer device according to claim 1, wherein said spacer device is made of biologically compatible material selected from among ceramics, resins with high porosity, plastic materials or a combination thereof, thermoplastic polymers, acrylic resins, polyethylene polypropylene, polyester, thermoformable polymers, bone cement, and polymethylmethacrylate (PMMA).

17. The spacer device according to claim 1, wherein said spacer device is porous and comprises at least one pharmaceutical or medical substance, including at least one antibiotic.

18. A method for the assembly of a spacer device for the articulation of the knee comprising the steps of:
providing a tibial component, adapted to be fixed to one end of a tibial bone in proximity to the knee joint, and
providing a femoral component, adapted to be fixed to one end of a femoral bone in proximity to the knee joint, wherein said femoral component has an opening and is adapted to come into contact and be articulated with said tibial component,
wherein said tibial component comprises a tibial plate provided with two condylar articular bases and a rib placed between said condylar articular bases, wherein said two condylar articular bases are adapted to come into contact and be articulated with said femoral component,
wherein said tibial component comprises a C-shaped protrusion and has a curved longitudinal axis and comprises a first section that corresponds with the rib, a second vertical section and a third section raised with respect to and parallel to the rib and terminating with a T-shaped head affixed at a distal end of the C-shaped protrusion, wherein said T-shaped head is integral with the C-shaped protrusion and comprises two opposing sections which each extend opposite from each other in a direction perpendicular with respect to the curved longitudinal axis of said C-shaped protrusion and wherein said opening comprises a first opening having width (L) and a second opening having width (N), wherein (L) is greater than (N); and
wherein the first section has a first end located at a terminal edge of the tibial plate and a second end meeting the second vertical section,
wherein said first section, said second vertical section and said third section define an opening having a longitudinal axis commencing from the terminal edge of the tibial plate to the second vertical section,
inserting said protrusion in said opening of said femoral component, to constrain said femoral component to said tibial component in a rotary manner and allow the sliding and rotation of said femoral component on said tibial component, wherein said inserting step comprises inserting the T-shaped head of said C-shaped protrusion into the first opening having width (L).

19. The method according to claim 18, wherein said femoral component has a box element having two internal lateral walls and one internal connector wall, wherein each internal lateral wall comprises a step, with overturned S-shaped conformation, wherein said method comprises the steps of sliding and rolling said sections on said step in a manner so as to allow the sliding and the rotation of said femoral component on said tibial component.

20. The method according to claim 18, comprising a step of providing a closure or locking element and closing said first opening by means of said closure or locking element, so as to prevent the exit of said protrusion from said opening of said femoral component.

* * * * *